United States Patent [19]

Elsheikh

[11] 4,329,482

[45] May 11, 1982

[54] PREPARATION OF MIXED CYCLOTETRASILOXANES AND ALIPHATIC CHLORIDES AND/OR ACYL CHLORIDES

[75] Inventor: Maher Y. A. I. Elsheikh, Midland, Mich.

[73] Assignee: Dow Corning Corporation, Midland, Mich.

[21] Appl. No.: 282,288

[22] Filed: Jul. 10, 1981

[51] Int. Cl.$^3$ .............................................. C07F 7/08
[52] U.S. Cl. .................................... 556/436; 556/460; 556/452; 556/461; 260/544 Y; 260/544 D; 260/544 L; 260/398; 260/408; 570/181; 570/189; 570/216; 423/325; 423/341
[58] Field of Search ............... 556/460, 436, 452, 461; 260/544 Y, 544 D, 544 L, 398, 408; 423/325, 341; 570/181, 189, 216

[56] References Cited

U.S. PATENT DOCUMENTS

| | | | |
|---|---|---|---|
| 2,610,199 | 9/1952 | Sommer | 556/436 |
| 2,721,856 | 10/1955 | Sommer | 556/436 X |
| 3,317,578 | 5/1967 | Prescott et al. | 260/448.2 |
| 3,328,345 | 6/1967 | Sporck | 260/46.5 |
| 3,347,895 | 10/1967 | Omietanski et al. | 260/448.2 |
| 3,358,009 | 12/1967 | Omietanski et al. | 260/448.2 |
| 3,391,109 | 7/1968 | Wilkus et al. | 556/436 X |
| 3,629,309 | 12/1971 | Bailey et al. | 556/436 X |

Primary Examiner—Paul F. Shaver
Attorney, Agent, or Firm—George A. Grindahl

[57] ABSTRACT

A method for preparing cyclotetrasiloxane, aliphatic chlorides and/or acyl chlorides from a cyclotrisiloxane, a chlorosilane and an acyloxy compound is disclosed. The chlorosilane and the acyloxy compound may be present as substantially equimolar amounts of separate compounds or they may be present in the same molecule in equimolar amounts. The reactants are merely heated sufficiently, with or without a soluble halide salt catalyst, to form the products. Advantageously this method can provide cyclotetrasiloxanes having water-sensitive radicals such as silicon-bonded chlorine atoms and/or silicon-bonded acyl chloride radicals. This method also provides a method for preparing cyclotetrasiloxanes having either one type of siloxane unit (nonmixed cyclotetrasiloxanes) or more than one type of siloxane unit (mixed cyclotetrasiloxanes).

18 Claims, No Drawings

PREPARATION OF MIXED CYCLOTETRASILOXANES AND ALIPHATIC CHLORIDES AND/OR ACYL CHLORIDES

BACKGROUND OF THE INVENTION

The present invention relates to a method for preparing cyclotetrasiloxanes from chlorosilanes without the concomitant formation of hydrogen chloride or hydrochloric acid. More specifically the present invention relates to a method for preparing cyclotetrasiloxanes, particularly mixed cyclotetrasiloxanes, by heating a mixture of a cyclotrisiloxane, a chlorosilane and an acyloxy compound and coproducing an aliphatic chloride and/or an acyl chloride.

Cyclotetrasiloxanes, particularly cyclotetradiorganosiloxanes such as octamethylcyclotetrasiloxane, are valuable materials because they can be further polymerized to prepare higher molecular weight silicone compositions, such as oils, gums and resins, and because they are useful, without further processing, as fluids.

Mixed cyclotetrasiloxanes, particularly mixed cyclotetradiorganosiloxanes such as heptamethylvinylcyclotetrasiloxane, are also valuable materials for the reasons give above and, additionally, because they can be polymerized to prepare higher molecular weight silicone copolymers having a specific composition and structure.

It is well known that dihydrocarbyldichlorosilanes can be hydrolyzed to prepare poly(dihydrocarbylsiloxanes) and hydrochloric acid. This method, although finding extensive commercial use, has several disadvantages. For example, the by-produced hydrochloric acid is an undesired by-product because it is corrosive, it cannot be used directly to form more dihydrocarbyldichlorosilane and it frequently reacts further with the hydrocarbyl radicals, such as methyl and vinyl radicals. Furthermore, this hydrolysis process does not produce only cyclopolysiloxanes, much less only cyclotetrasiloxanes, but rather a mixture of various linear and cyclic polysiloxanes. Also, this hydrolysis process cannot be used to prepare cyclopolysiloxanes bearing water-sensitive radicals such as silicon-bonded chlorine atoms or acyl chloride radicals. Additionally, this hydrolysis process cannot be used to prepare mixed cyclotetrasiloxanes having a specific composition, because the random joining of hydrolyzed silane molecules forms random siloxanes and, hence, random cyclotetrasiloxanes.

Speier, in an application for U.S. patent, titled "Preparation of Cyclotetrasiloxanes and Aliphatic Chlorides and/or Acyl Chlorides", Ser. No. 282,289, assigned to the assignee of this invention and filed on July 10, 1981, claims a method for preparing cyclotetrasiloxanes which has many advantages over the processes of the art and avoids many of the disadvantages of the processes of the art. The method of Speier does not coproduce hydrogen chloride or hydrochloric acid; but, rather, an aliphatic chloride and/or an acyl chloride. In addition to cyclotetrasiloxanes having water-insensitive radicals, the method of Speier also provides cyclotetrasiloxanes which bear silicon-bonded radicals which are water-sensitive, such as chlorine atoms and acyl chloride radicals. However, the method of Speier cannot provide mixed cyclotetrasiloxanes having a specific composition.

Other methods for preparing cyclotetrasiloxanes have been disclosed in the art. Generally these methods comprise the condensation reaction of a silane reactant with a linear trisiloxane reactant and are exemplified by the disclosure of U.S. Pat. No 3,317,578; 3,328,345; 3,347,895 and 3,358,009. Typically, one of the reactants contains silicon-bonded chlorine atoms and the other reactant contains silicon-bonded hydroxyl radicals, the inter-reaction of which produces hydrogen chloride and the desired cyclotetrasiloxane. As noted above hydrogen chloride is an undesirable by-product; it is in these processes as well. Additionally, the cited patents teach that the by-produced hydrogen chloride leads to the formation of linear siloxanes at the expense of the desired cyclotetrasiloxane unless it is immediately removed from the reaction mixture; a requirement that is difficult to meet or that produces additional disadvantages. For example, rapid removal of hydrogen chloride can be achieved by using an amine in the reaction mixture as an HCl scavenger; however, the resulting amine hydrochloride salt is difficult to remove. On the other hand, HCl can be removed by aeration or boiling; however, this is a relatively slow method of removing HCl and undesirable acid catalyzed reactions of the cyclotetrasiloxanes often occur. Additionally, this condensation reaction method for producing cyclotetrasiloxane has the further disadvantage of being unsuitable for preparing cyclotetrasiloxanes which bear silicon-bonded acyl chloride radicals because they react with silicon-bonded hydroxyl radicals.

BRIEF SUMMARY OF THE INVENTION

It is an object of the present invention to provide a method for preparing cyclotetrasiloxanes, as substantially the sole polysiloxane product, from chlorosilanes. It is another object of this invention to provide a method for preparing cyclotetrasiloxanes from chlorosilanes that does not co-produce hydrogen chloride or hydrochloric acid. It is a further object of this invention to provide a method for preparing cyclotetrasiloxanes that bear water-sensitive, silicon-bonded radicals; especially silicon-bonded acyl chloride-substituted hydrocarbon radicals. It is yet another object of this invention to provide a method for preparing cyclotetrasiloxanes from chlorosilanes while coproducing an aliphatic chloride and/or an acyl chloride. It is also an object of this invention to provide a process for preparing acyl chlorides and aliphatic chlorides from aliphatic esters of hydrocarbon acids. It is yet another object of this invention to provide a method for preparing mixed cyclotetrasiloxanes.

These objects, and others which will become obvious to one of ordinary skill in the siloxane synthesis art upon considering the following disclosure and appended claims, are obtained by the method of this invention, which, broadly characterized, comprises heating a mixture comprising a cyclotrisiloxane and a silane-acyloxy component comprising equimolar amounts of a silane reaction site bearing at least two silicon-bonded chlorine atoms and a hydroxyl-free acyloxy reaction site. Depending on the desired reaction products the silane reaction site and the acyloxy reaction site can be part of the same molecule or of separate molecules. The reaction of this invention can furthermore be facilitated by the use of catalytic amounts of a halide salt catalyst possessing sufficient solubility in the reaction mass during the heating process.

Herein the terms mixed and non-mixed, when applied to cyclopolysiloxanes such as cyclotrisiloxanes and cyclotetrasiloxanes, refers to the siloxane units, not to the radicals, of the cyclopolysiloxane. For example, {(CH$_3$)$_2$SiO}$_4$ and {(CH$_3$)(C$_6$H$_5$)SiO}$_4$ are non-mixed cyclotetrasiloxanes because all siloxane units therein are identical in structure. An example of a mixed cyclotetrasiloxane is {(CH$_3$)$_2$SiO}$_3${(CH$_3$)(CH$_2$=CH)SiO} because all siloxane units therein are not identical in structure.

DETAILED DESCRIPTION OF THE INVENTION

The present invention relates to a method for preparing a cyclotetrasiloxane and an aliphatic chloride and/or an acyl chloride, said method comprising heating a mixture consisting essentially of (I) one molar portion of a silane-acyloxy compound selected from the group consisting of (A) a silylhydrocarbonoxy acylate having the formula R$^1_a$Cl$_{(3-a)}$SiQO$_2$CR$^2$, (B) a hydrocarbonoxy silylacylate having the formula R$^1_a$Cl$_{(3-a)}$SiQCO$_2$R$^2$ and (C) a mixture of equimolar amounts of (i) a silane having the formula R$^1_b$SiCl$_{(4-b)}$ and (ii) an acyloxy compound selected from the group consisting of hydrocarbon carboxylic esters and hydrocarbon carboxylic anhydrides, wherein, at each occurance, a denotes a number having a value of 0 or 1; b denotes a number having a value of 0, 1 or 2; R$^1$ denotes a monovalent substituted or unsubstituted hydrocarbon radical; R$^2$ denotes a monovalent unsubstituted hydrocarbon radical; Q denotes a divalent substituted or unsubstituted hydrocarbon radical; any hydrocarbon radical bonded to an oxygen atom of an acyloxy radical being bonded at an aliphatic carbon of said any hydrocarbon radical and (II) at least one molar portion of a cyclotrisiloxane having the formula (R$^1_2$SiO—)$_3$ wherein each R$^1$ denotes, independently, a monovalent substituted or unsubstituted hydrocarbon radical; said heating being sufficient to produce a cyclotetrasiloxane having the formula

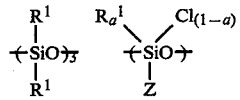

wherein R$^1$ and a are as denoted above and Z denotes a radical selected from the group consisting of R$^1$, Cl, QCOCl and QCl and at least one reaction product selected from the group consisting of an acyl chloride and an aliphatic chloride; the substituents of said substituted hydrocarbon radicals being non-reactive during said heating. Herein cyclic polysiloxane are written in lineformula form with the ring-completing bond being omitted for simplicity. For example,

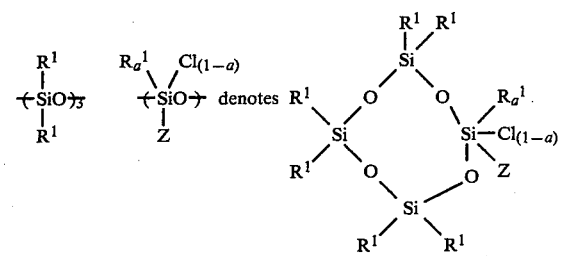

The present invent relates further to cyclotetrasiloxanes having the formula (R$^1_2$SiO—)$_3$(R$^1$QCOClSiO—wherein R$^1$ and Q are as denoted above.

The silane-acyloxy component (I) to be used in the method of this invention consists of equimolar amounts of a silane reaction site and an acyloxy reaction site. By equimolar amounts it is meant molar amounts that provide no more than about a 10 percent molar excess of either reaction site. Thus the molar ratio of silane reaction site to acyloxy reaction site has a value of from about 0.9/1.0 to about 1.1/1.0.

The silane reaction site and the acyloxy reaction site can be in the same molecular or in separate molecules, thereby giving rise to two aspects of this invention. In each aspect the reaction products that are produced by the method of this invention comprise a cyclotetrasiloxane and an aliphatic chloride and/or an acyl chloride.

In one aspect of this invention the silane reaction site and the acyloxy reaction site are present in the same molecule to provide a silane-acyloxy component (I) consisting essentially of a silylhydrocarbonoxy acylate having the formula (A) or a hydrocarbonoxy silylacylate having the formula (B).

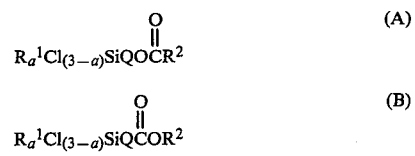

When a mixture of a cyclotrisiloxane (R$^1_2$SiO—)$_3$ and component (A) is heated sufficiently an aliphatic chloride-substituted cyclotetrasiloxane having the formula

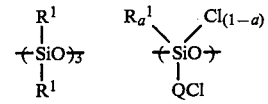

and an acyl chloride having the formula R$^2$COCl are formed.

When a mixture of a cyclotrisiloxane (R$^1_2$SiO—)$_3$ and component (B) is heated sufficiently an acyl chloride-substituted cyclotetrasiloxane having the formula

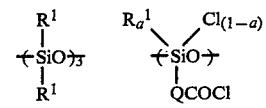

and an aliphatic chloride having the formula R$^2$Cl are obtained.

In formulae (A) and (B) a denotes a number having a value of 0 or 1, thereby requiring 3 or 2, respectively, silicon-bonded chlorine atoms for every silicon atom in the silane-acyloxy component. Preferably a has a value of 1 thereby providing, after heating, valuable mixed cyclotetrasiloxanes which are free of silicon-bonded chlorine atoms. Advantageously, when a has a value of 0 mixed cyclotetrasiloxanes bearing silicon-bonded chlorine atoms are obtained which are otherwise difficult to obtain.

In silane-acyloxy component (A) and (B) the silane reaction site is bonded to the acyloxy reaction site by way of a divalent hydrocarbon radical Q. This Q radical is bonded by one of its valences to the silicon atom at either an aliphatic or aromatic carbon atom of the Q radical, and by its remaining valence to the acyloxy oxygen atom in (A) at an aliphatic carbon atom of the Q radical or to the acyloxy carbon atom in (B) at either an aliphatic or aromatic carbon atom of the Q radical. This bonding is required because a silane-acyloxy component wherein the acyloxy reaction site contains a

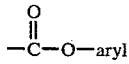

linkage is not sufficiently reactive to produce the desired reaction products.

Unsubstituted divalent hydrocarbon radicals contemplated by Q include aliphatic radicals; such as alkylene radicals having the formula $-C_nH_{2n}-$, wherein n is a positive integer, such as $-CH_2-$, $-CH_2CH_2-$, $-\overset{.}{C}CH_3$, $-CH_2CH_2CH_2-$, $-CH_2\overset{.}{C}HCH_3$, $-CH_2CH_2CH_2CH_2-$, $-CH_2CH_2\overset{.}{C}HCH_3$, $-(CH_2)_8-$ and $-CH_2CH(CH_2CH_3)CH_2CH_2CH_2CH_2-$; and cycloaliphatic radicals, such as cyclohexylene; and aromatic radicals; such as $-Ay-$, $-AyCH_2-$, $-AyCH_2CH_2-$, $-CH_2AyCH_2-$, $-CH_2CH_2AyCH_2CH_2-$, $-CH_2CH(Ph)CH_2-$ and $-CH_2\overset{.}{C}H(Ph)$ wherein Ay denotes the phenylene radical and Ph denotes the phenyl radical. Said divalent hydrocarbon radicals contemplated for Q can also bear aliphatic unsaturation such as is found in $-CH_2CH=CHCH_2-$, cyclohexenylene and $-CH_2\overset{.}{C}HCH=CH_2$.

Preferably Q is an unsubstituted alkylene radical having the formula $-C_nH_{2n}-$ wherein n has a value of from 2 to 4, such as $-CH_2CH_2-$, $-CH_2CH_2CH_2-$, $-CH_2\overset{.}{C}HCH_3$, $-CH_2CH_2CH_2CH_2-$ and $-CH_2CH_2\overset{.}{C}HCH_3$.

Substituted divalent hydrocarbon radicals contemplated by Q include the unsubstituted divalent hydrocarbon radicals contemplated above wherein one or more hydrogen atoms have been replaced by a substituent which is non-reactive during the heating step in the method of this invention. Examples of said substituents include halogen, preferably chlorine and fluorine, nitro and cyano. Preferably said substituent is separated from the silicon atom by at least 3 carbon atoms.

In silane-acyloxy component (A) and (B) $R^1$ denotes a monovalent substituted or unsubstituted hydrocarbon radical and $R^2$ denotes a monovalent unsubstituted hydrocarbon radical. As noted above for any Q radical bonded to an acyloxy oxygen atom, when $R^2$ is bonded to an acyloxy oxygen atom it is bonded thereto at an aliphatic carbon atom of the $R^2$ radical. When $R^2$ is bonded to the acyloxy carbon atom, it can be bonded thereto at an aliphatic or aromatic carbon atom of the $R^2$ radical.

Unsubstituted monovalent hydrocarbon radicals contemplated by $R^1$ and $R^2$ include any hydrocarbon radical having from 1 to 18 carbon atoms, preferably 1 to 6 carbon atoms, such as alkyl radicals, such as methyl, ethyl, propyl, isopropyl, butyl, isobutyl, hexyl, 2-ethylhexyl, octyl, decyl and octadecyl; alkenyl radicals, such as vinyl and allyl; alkynyl radicals; such as propargyl; cycloaliphatic radicals, such as cyclohexyl and cyclohexenyl; aryl radicals, such as phenyl, naphthyl, tolyl, xylyl and xenyl; and aralkyl radicals, such as benzyl, beta-phenylethyl, beta-phenylpropyl and gamma-tolylpropyl. Most preferably $R^1$ is the methyl radical and $R^2$ is a lower alkyl radical, such as methyl, ethyl, propyl, butyl, isopropyl and isobutyl.

Substituted monovalent hydrocarbon radicals contemplated by $R^1$ include the unsubstituted monovalent hydrocarbon radicals contemplated above wherein one or more hydrogen atoms have been replaced by a substituent which is non-reactive during the heating step in the method of this invention. Examples of said substituents include halogen, preferably chlorine and fluorine, nitro and cyano. Preferably said substituent is a halogen atom and is separated from the silicon atom by at least 3 carbon atoms.

Examples of substituted monovalent hydrocarbon radicals contemplated by $R^1$ include $-CH_2CH_2CH_2Cl$, $-CH_2CH_2CF_3$, $-AyCl$, $-AyNO_2$ and $-CH_2CH(CH_3)CH_2Cl$.

Herein Ay, Ph, $Pr_f$, $Pr_{Cl}$, Vi and $Bu_{Cl}$ denote, respectively, $-C_6H_4-$, $C_6H_5-$, $CF_3CH_2CH_2-$, $ClCH_2CH_2CH_2$, $CH_2=CH-$ and $ClCH_2CH(CH_3)CH_2-$.

Examples of silane-acyloxy component (A) which are suitable for use in the method of this invention include, but are not limited to, the following:
$Cl_3SiCH_2CH_2CH_2O_2CCH_3$, $Cl_3SiCH_2CH_2CH_2O_2CCH_2CH_3$, $CH_3(Cl)_2SiCH_2CH(CH_3)CH_2O_2CCH_3$, $CH_3(Cl)_2SiCH_2CH(CH_3)CH_2O_2CCH_2CH_3$, $CH_3(Cl)_2SiCH_2CH_2CH_2O_2CCH_2CH_3$, $CH_3(Cl)_2SiCH_2CH_2CH_2O_2CCH_3$, $Ph(Cl)_2SiCH_2CH_2CH_2O_2CCH_3$, $Ph(Cl)_2SiCH_2CH(CH_3)CH_2O_2CCH_3$, $Vi(Cl)_2SiCH_2CH_2CH_2O_2CCH_3$, $Vi(Cl)_2SiCH_2CH_2CH_2O_2CCH_2CH_3$, $Pr_f(Cl)_2SiCH_2CH_2CH_2O_2CCH_3$, $Pr_f(Cl)_2SiCH_2CH_2CH_2O_2CCH(CH_3)_2$, $Pr_{Cl}(Cl)_2SiCH_2CH_2CH_2O_2CCH_3$, $Pr_{Cl}(Cl)_2SiCH_2CH_2CH_2O_2CCH_2CH_3$, $CH_3(Cl)_2SiCH_2CH_2CH_2O_2CC(CH_3)_3$, $CH_3(Cl)_2SiCH_2CH_2CH_2O_2CCH(CH_3)_2$, $CH_3(Cl)_2SiCH_2CH_2CH_2O_2CPh$, $Bu_{Cl}(Cl)_2SiCH_2CH_2CH_2O_2CCH_3$, and $Bu_{Cl}(Cl)_2SiCH_2CH_2CH_2O_2CCH_2CH_3$.

Examples of silane-acyloxy component (B) which are suitable for use in the method of this invention include, but are not limited to, the following:
$Cl_3SiCH_2CH_2CH_2CO_2CH_3$, $Cl_3SiCH_2CH(CH_3)CH_2CO_2CH_2CH_3$, $Cl_3SiAyCO_2CH_3$, $CH_3(Cl)_2SiCH_2CH(CH_3)CH_2CO_2CH_3$, $CH_3(Cl)_2SiCH_2CH_2CH_2CO_2CH_3$, $CH_3(Cl)_2SiCH_2CH(CH_3)CH_2CO_2CH_2CH_3$, $CH_3(Cl)_2SiCH_2CH_2CH_2CO_2CH_2CH_3$, $Ph(Cl)_2SiCH_2CH_2CH_2CO_2CH_3$, $Ph(Cl)_2SiCH_2CH(CH_3)CH_2CO_2CH_3$, $Vi(Cl)_2SiCH_2CH_2CH_2CO_2CH_3$, $Vi(Cl)_2SiCH_2CH_2CH_2CO_2CH_2CH_3$, $Pr_f(Cl)_2SiCH_2CH_2CH_2CO_2CH_3$, $Pr_f(Cl)_2SiCH_2CH_2CH_2CO_2CH(CH_3)_2$, $Pr_{Cl}(Cl)_2SiCH_2CH_2CH_2CO_2CH_3$, $Pr_{Cl}(Cl)_2SiCH_2CH_2CH_2CO_2CH_2CH_3$, $CH_3(Cl)_2SiCH_2CH_2CH_2CO_2C(CH_3)_3$, $CH_3(Cl)_2SiCH_2CH_2CH_2CO_2CH_3$, $CH_3(Cl)_2SiAyCO_2CH_3$, $CH_3(Cl)_2SiCH_2CH(CH_3)CO_2CH_3$, $Bu_{Cl}(Cl)_2SiCH_2CH_2CH_2CO_2CH_3$, $Bu_{Cl}(Cl)_2SiCH_2CH_2CO_2CH_2CH_3$ and $Bu_{Cl}(Cl)_2SiCH_2CH(CH_3)CO_2CH_3$.

Silane-acyloxy component (A) and (B) can be prepared by any suitable method. Preferably a suitable chlorohydrosilane is added to a suitable aliphatically unsaturated acyloxy compound in a hydrosilylation reaction. Preferably the hydrosilylation reaction is catalyzed by a platinum-containing catalyst.

By way of example, CH₃(Cl)₂SiH can be added to CH₂=C(CH₃)CO₂CH₃ in a hydrosilylation reaction to provide CH₃(Cl)₂SiCH₂CH(CH₃)CO₂CH₃ or to CH₂=CHCH₂O₂CCH₃ to provide CH₃(Cl)₂SiCH₂CH₂CH₂O₂CCH₃. Hydrosilylation is a well-known synthesis reaction in the organosilicon art and needs no further elaboration herein. Analogously, other silane-acyloxy components (A) and (B) contemplated herein can be synthesized from the appropriate chlorohydrosilane and the appropriate aliphatically unsaturated acyl compound. Other suitable synthesis methods and schemes will be obvious to one skilled in the organosilicon art.

In another aspect of this invention the silane reaction site and the acyloxy reaction site are present in separate molecules to provide a silane-acyloxy component (C) consisting essentially of a mixture of equimolar amounts of a silane (i) having the formula R¹$_b$SiCl$_{(4-b)}$ and an acyloxy compound (ii) selected from the group consisting of hydrocarbon carboxylic esters and hydrocarbon carboxylic anhydrides.

When a mixture of cyclotrisiloxane (R¹₂SiO)₃ and silane-acyloxy component (C) is heated sufficiently a cyclotetrasiloxane having the formula

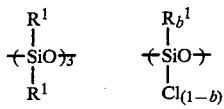

is formed along with an acyl chloride and, additionally when (ii) is a hydrocarbon carboxylic ester, an aliphatic chloride.

In the formula for silane (i) which forms a part of silane-acyloxy component (C) b denotes a number having a value of 0, 1 or 2, thereby requiring 4, 3 or 2, respectively, silicon-bonded chlorine atoms for every silicon atom in the silane. Preferably b has a value of 2, thereby providing, after heating, valuable cyclotetradiorganosiloxanes, either mixed or not mixed, which are free of silicon-bonded chlorine atoms. Advantageously, when b has a value of 0 or 1 cyclotetrasiloxanes, either mixed or not mixed, bearing silicon-bonded chlorine atoms are obtained which are otherwise difficult to obtain.

In the formula for silane (i) each R¹ denotes, independently, any of the substituted and unsubstituted monovalent hydrocarbon radicals contemplated or indicated as being preferred or delineated above for silane-acyloxy component (A) and (B). The methyl radical is a preferred unsubstituted R¹ radical and halogenated radicals are preferred substituted R¹ radicals in silane (i).

Examples of silane (i) which are suitable for use in this second aspect of the method of this invention include, but are not limited to, the following: SiCl₄, CH₃SiCl₃, PhSiCl₃, Pr$_f$SiCl₃, Pr$_{Cl}$SiCl₃, ViSiCl₃, Bu$_{Cl}$SiCl₃, (CH₃)₂SiCl₂, CH₃(Vi)SiCl₂, CH₃(Ph)SiCl₂, CH₃(Pr$_f$)SiCl₂, CH₃(Pr$_{Cl}$)SiCl₂, CH₃(Bu$_{Cl}$)SiCl₂, (Ph)₂SiCl₂, (Ph)(Vi)SiCl₂, (Ph)(Pr$_f$)SiCl₂, (Ph)(Pr$_{Cl}$)SiCl₂ and (Ph)(Bu$_{Cl}$)SiCl₂.

Many silanes encompassed by (i) are well-known materials whose synthesis needs no further elaboration herein. Suffice it to say that several can be prepared by the direct reaction of a hydrocarbon halide with elemental silicon in the well-known manner. Advantageously the method of this invention can provide desired aliphatic chlorides which can be used in said direct reaction.

Other silanes encompassed by (i) can be prepared by the well-known reaction of an aliphatically unsaturated material; such as an olefin, such as CH₂=CH₂, CH₂=CHCH₃, CH₂=CHCF₃, CH₂=CHCH₂Cl and CH₂=CH(CH₃)CH₂Cl and a suitable chlorohydrosilane; such as CH₃(Cl)₂SiH, Ph(Cl)₂SiH, Cl₃SiH and Cl₂SiH₂.

Acyloxy compound (ii) which forms a part of silane-acyloxy component (C) can be any hydrocarbon carboxylic ester, which contains a

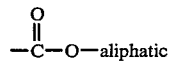

linkage, or any hydrocarbon carboxylic anhydride. Acyloxy compound (ii) can have an open chain structure or a cyclic structure. Accordingly, acyloxy compound (ii) contemplates esters having the formula

lactones having the formula

and anhydrides having the formulae

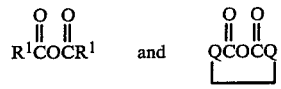

wherein R¹ and Q have the meanings denoted above. Preferably acyloxy compound (ii) has the formula

wherein R² has the meaning denoted above.

Examples of acyloxy compounds (ii) which are suitable for use in this second aspect of the method of this invention include, but are not limited to, the following: CH₃CO₂CH₃, CH₃CO₂CH₂CH₃, CH₃CO₂CH(CH₃)₂, CH₃CO₂C(CH₃)₃, CH₃CH₂CO₂CH₃, CH₃CH₂CO₂CH₂CH₃, (CH₃)₃CCO₂CH₃, PhCO₂CH₃, PhCO₂CH₂CH₃, CH₂=C(CH₃)CO₂CH₃, CH₃CO₂CH₂Ph, (CH₃CO)₂O,

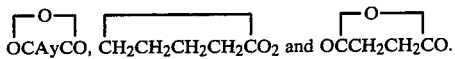

Most preferably acyloxy compound (ii) is an ester having the formula R²CO₂R² wherein each R² denotes, independently, a lower alkyl radical, such as methyl, ethyl, propyl, ispropyl and tertiary butyl.

Component (II) that is used in the method of this invention can be any cyclotrisiloxane having the formula (R¹₂SiO)₃. In said cyclotrisiloxane the R¹ radicals can be any of the monovalent substituted or unsubstituted hydrocarbon radicals contemplated or indicated as being preferred or delineated above for the $R^1$ radicals of silane-acyloxy component (I).

The cyclotrisiloxane can have $R^1$ radicals which are all the same. For example, in a preferred embodiment of this invention the cyclotrisiloxane is $\{(CH_3)_2SiO\}_3$ thereby providing a cyclotetrasiloxane reaction product wherein three of the four siloxane units are dimethylsiloxane units. The fourth siloxane unit of the cyclotetrasiloxane reaction product can be a dimethylsiloxane unit, thereby providing a non-mixed cyclotetrasiloxane, or a different siloxane unit, thereby providing a mixed cyclotetrasiloxane, depending upon the silane-acyloxy component (I) that is used.

The cyclotrisiloxane can have $R^1$ radicals which are not all the same. For example, the cyclotrisiloxane can be a non-mixed cyclotrisiloxane, such as $\{(CH_3)(CF_3CH_2CH_2)SiO\}_3$, thereby providing a cyclotetrasiloxane reaction product wherein three of the four siloxane units are methyl-3,3,3-trifluoropropylsiloxane units. The fourth siloxane unit of the cyclotetrasiloxane reaction product can be a methyl-3,3,3-trifluoropropylsiloxane unit, thereby providing a non-mixed cyclotetrasiloxane, or a different siloxane unit, thereby providing a mixed cyclotetrasiloxane, depending upon the silane-acyloxy component (I) that is used.

In another example of a cyclotrisiloxane having $R^1$ radicals which are not all the same the cyclotrisiloxane can be a mixed cyclotrisiloxane, such as $\{(C_6H_5)_2SiO\}_2\{(CH_3)_2SiO\}$. In this example only mixed cyclotetrasiloxanes are obtained from the method of this invention, regardless of the particular silane-acyloxy component (I) that is used.

Examples of mixed cyclotrisiloxanes (II) which are suitable for use in both aspects, denoted above, of this invention include, but are not limited to the following:
$\{(Ph)_2SiO\}_2\{(CH_3)_2SiO\}$, $\{(CH_3)(Vi)SiO\}_2\{(CH_3)_2SiO\}$, $\{(Ph)_2SiO\}_2\{(CH_3)(Ph)SiO\}$ and $\{(CH_3)_2SiO\}_2\{(CH_3)(Pr_f)SiO\}$.

Examples of non-mixed cyclotrisiloxanes (II) which are suitable for use in both aspects, denoted above, of this invention include, but are not limited to, the following:
$\{(CH_3)_2SiO\}_3$, $\{(CH_3CH_2)_2SiO\}_3$, $\{(Ph)_2SiO\}_3$, $\{(Vi)_2SiO\}_3$, $\{(CH_3)(CH_3CH_2)SiO\}_3$, $\{(CH_3)(Ph)SiO\}_3$, $\{(CH_3)(Pr_f)SiO\}_3$, $\{(CH_3)(Pr_{Cl})SiO\}_3$, $\{(CH_3)(Vi)SiO\}_3$, $\{(Pr_f)(Vi)SiO\}_3$, $\{(Ph)(Pr_f)SiO\}_3$, $\{(Ph)(Vi)SiO\}_3$, $\{(CH_3)(Bu_{Cl})SiO\}_3$ and $\{(CH_3)(AyCl)SiO\}_3$.

Mixed and non-mixed cyclotrisiloxanes (II) can be prepared by any suitable method; such as by the condensation of a difunctional silane with a difunctional disiloxane as disclosed in U.S. Pat. Nos. 3,317,578; 3,328,346 and 3,347,895; by the hydrolysis, condensation and equilibration of a suitable dichlorosilane such as $(CH_3)_2SiCl_2$ and subsequent fractional distillation of the most volatile cyclotrisiloxane species; or by the hydrosilylation reaction of an olefin, such as $CF_3CH=CH_2$ and a silicon-hydride containing cyclotrisiloxane such as $\{(CH_3)(H)SiO\}_3$.

In the method of this invention the mixture to be heated consists essentially of one molar portion of the silane-acyloxy component (I) and at least one molar portion of the cyclotrisiloxane component (II). By one molar portion of the silane-acyloxy component it is meant one molar portion of the silylhydrocarbonoxy acylate (A) or of the hydrocarbonoxy silylacylate (B) or a sufficient amount of silane-acyloxy component (C) comprising an equimolar mixture of silane (i) and acyloxy compound (ii) to provide one molar portion of the silane (i) or of the acyloxy compound (ii), or both.

When an equimolar portion of cyclotrisiloxane component is mixed for every molar portion of silane-acyloxy component there is produced up to one molar portion of the cyclotetrasiloxane reaction product. When greater than an equimolar portion of cyclotrisiloxane component is mixed for every molar portion of silane-acyloxy component there is produced up to one molar portion of the cyclotetrasiloxane reaction product mixed with unreacted cyclotrisiloxane.

In the method of this invention the mixture of (I) and (II) is heated sufficiently to provide the desired cyclotetrasiloxane and aliphatic chloride and/or acyl chloride reaction products. By heated sufficiently it is meant the use of any combination of temperature and time that will provide the desired results.

The amount of heating that is sufficient will depend upon the particular mixture that is being heated and whether or not said mixture further comprises an effective amount of a halide salt catalyst, delineated below. Generally, heating at temperatures greater than 200° C. for a period of time exceeding 15 hours is required to produce significant amounts of desired reaction products when said catalyst is not present. The use of a catalyst permits the use of less-vigorous heating; significant, and sometimes quantitative, yields of desired reaction product being obtained with heating at for example at room temperature for 6 hours, or 100° C. for 2 hours, or at 130° C. for 0.3 hours. Sufficient heating can be readily determined by routine experimentation, especially after one considers the examples disclosed herein.

The method of this invention can be performed at any pressure such as at subatmospheric, atmospheric or superatmospheric pressure and in either a closed or open system. Preferably the more-volatile reaction mixtures are heated in a pressure system and the less-volatile reaction mixtures are heated in a vented system. The particular method of heating the reaction mixture is not critical and one of ordinary engineering skill will be able to devise a particular system to achieve typical production goals such as continuous or batch processing, continuous removal of a particular reaction product from the reaction zone, recycling of unspent reactants and catalyst and the like.

The process of this invention is facilitated by the use of a catalytic amount of a halide salt. Any halide salt which has appreciable solubility in the reaction mixture during the heating thereof is effective in the method of this invention. Iodide salts are more effective than bromide salts which are more effective than chloride salts. Quaternary ammonium, pyridinium and phosphonium halides are preferred halide salts because of their appreciable solubility in the reaction mixture. Metal halides, such as $AlCl_3$ and $ZnCl_2$, having appreciable solubility in the heated reaction mixture are also effective catalysts in the method of this invention.

Examples of halide catalysts which are suitable for use in the method of this invention include, but are not limited to, the following: quaternary ammonium halides, such as $Bu_4NBr$, $Bu_4NCl$, $Bu_4NI$; quaternary pyridinium halides, such as $C_5H_5(CH_3)NCl$, $C_5H_5(CH_3)NBr$, $C_5H_5(CH_3)NI$, $C_5H_5(CH_3CH_2)NCl$, $C_5H_5(CH_3)(CH_2)NBr$, $C_5H_5(CH_3CH_2)NI$ and those disclosed by Mahone, U.S. Pat. No. 4,108,882; quaternary phosphonium halides, such as $Bu_4PCl$ and $Bu_4PBr$ and metal halides, such as $AlCl_3$.

The amount of the halide catalyst to be used is typically from about 0.1 to 10, preferably 1 to 5 percent by weight based on the weight of the reaction mixture.

The cyclotetrasiloxanes provided by the method of this invention have all the uses of cyclotetrasiloxanes that are prepared by methods of the art. They can be used, per se, where siloxane fluids are used, and they can also be used to prepare linear and branched homopolymeric and copolymeric polysiloxane fluids, gums and resins. This invention provides a preferred method for preparing mixed cyclotetrasiloxanes, such as $\{(CH_3)_2SiO\}_3\{(CH_3)(CH_2=CH)SiO\}$ and the novel $\{(CH_3)_2SiO\}_3$ $\{(CH_3)(ClOCCH_2CH(CH_3)CH_2)SiO\}$, which cannot be obtained from the hydrolysis of the corresponding mixture of dichlorosilanes.

The method of this invention also provides valuable aliphatic chlorides and acyl chlorides which would be difficult to synthesize by other routes. Advantageously, the aliphatic chlorides can be used directly to prepare valuable silane intermediates.

The following examples are disclosed to further illustrate, but not to limit, the present invention.

H-n.m.r. spectra were recorded either with a Varian A-60 or a Varian EM-390 instrument and are reported in p.p.m., using tetramethysilane as an internal reference.

Infrared spectra were obtained with a Beckman Acculab 2 spectrophotometer.

Gas-liquid chromatograms (g.l.c.) were obtained with a Hewlett Packard Model HP 5710A chromatograph, fitted with $10' \times \frac{1}{8}''$ stainless steel columns packed with Chromosorb W-HP 100/120 mesh containing 15% by weight OV 101 as the liquid phase, and coupled with a Hewlett Packard Model HP 3380A integrator.

Percent conversion means g.l.c. area percent based on the entire peak area of the chromatogram. Percent yield means weight percent of product obtained based on weight of starting material that reacted.

EXAMPLE 1

A mixture of $Cl_2CH_3SiCH_2CH(CH_3)CO_2CH_3$, 2.0 g. (9.3 m mols); $(Me_2SiO)_3$, 2.0 g. (9.0 m mols); and Bu$_4$NBr, 0.14 g. was heated in a vented flask at 160° C. for 5 hours. Substantially pure (97%) CH$_3$Cl was rapidly evolved. After the reactants had completely reacted the oily residue in the flask was determined by H' n.m.r. to be the mixed cyclotetrasiloxane $(Me_2SiO)_3(MeRSiO)$ where R denotes the $-CH_2CH(CH_3)COCl$ radical. The n.m.r. spectrum(δ) was 0.2 (SiCH$_3$, 21H, s); 0.8 (CH$_2$, 2H, m); 1.4 (C—CH$_3$, 3H, d, J=7 Hz); 2.6 (CH, 1H, m).

As a comparison experiment this reaction was repeated using 1.5 g. (7.0 m mols) of the silane, 5.2 g. (17.5 m mols) of $(Me_2SiO)_4$ instead of $(Me_2SiO)_3$ and 0.02 g. Bu$_4$NBr; no reaction occurred.

In a control experiment a mixture of $(Me_2SiO)_3$ and Bu$_4$NBr was heated at 155° C. for 8 hrs; no reaction occurred.

EXAMPLE 2

A mixture of $Cl_2CH_3SiCH_2CH(CH_3)CO_2CH_3$, 2.0 g. (9.3 m mols); $(Me_2SiO)_3$, 4.2 g. (18.9 m mols); and Bu$_4$NBr, 0.005 g. was heated in a sealed ampoule at 140° C. for 3 hours. N.m.r. analysis of the reaction mixture showed that over 98% of the starting silane compound, and a substantial portion of the starting siloxane compound, were converted to the product described in Example 1.

EXAMPLE 3

Example 1 was repeated using 250 g. (1.16 mols) of the silane, 257.98 (1.16 mols) of the cyclotrisiloxane and 7.5 g. (1.5 w%) of Bu$_4$NBr; a nearly quantitative yield of the described product was obtained.

EXAMPLE 4

A mixture of Me$_2$SiCl$_2$, 1.9 g (15 m mols); CH$_3$CO$_2$CH$_3$, 1 g. (13 m mols); $(Me_2SiO)_3$, 4 g. (18 m mols); and Bu$_4$NBr, 0.14 g. was heated in a sealed ampoule at 200° C. for 2 hours. G.l.c. analysis showed a 67% conversion of Me$_2$SiCl$_2$ and $(Me_2SiO)_3$ to $(Me_2SiO)_4$ and a trace amount of $(Me_2SiO)_5$.

In a control experiment a mixture of $(Me_2SiO)_3$ and Bu$_4$NBr was heated in a sealed ampoule at 200° C. for 15 hours; no reaction occurred.

EXAMPLE 5

A mixture of $Cl_3SiCH_2CH_2CH_2O_2CCH_3$, 2 g. (9.5 m mols); $(Me_2SiO)_3$, 4 g. (18 m mols); and Bu$_4$NBr, 0.3 g. (5 w%) was heated in a sealed ampoule at 200° C. for 1.5 hours. G.l.c. analysis of the reaction product showed nearly complete reaction of the silane, excess unreacted $(Me_2SiO)_3$, CH$_3$COCl and a higher boiling product. The acetyl chloride and unreacted cyclotrisiloxane were distilled from the reaction products to leave 2.6 g. (84% yield) of the mixed cyclotetrasiloxane $(Me_2SiO)_3(ClRSiO)$, where R denotes $-CH_2CH_2CH_2-$.

EXAMPLE 6

A mixture of $Cl_3SiCH_2CH_2CH_2O_2CCH_3$, 2 g. (8.5 m mols); $(Me_2SiO)_3$, 4 g. (18 m mols); Bu$_4$NBr, 0.3 g. (5 w%) and CCl$_4$, 4 ml. was shaken in a bottle at room temperature for 20 hours. G.l.c. analysis showed unreacted starting materials and the reaction product $(Me_2SiO)_3(ClRSiO)$ where R denotes $-CH_2CH_2CH_2-$.

EXAMPLE 7

Hexamethylcyclotrisiloxane (4 g., 0.018 mole), methylvinyldichlorosilane (2 g., 0.014 mole), t-butyl acetate (1.1 g., 0.01 mole) and tetrabutylammonium bromide (0.03 g.) were stirred together for six hours at room temperature and analyzed by g.l.c. Only three products showed as peaks on the g.l.c. graph. They corresponded to acetyl chloride, t-butyl chloride and pentamethylvinylcyclotetrasiloxane. The mixture had reacted about 25% in 6 hours at room temperature to form the 3 products in 100% yield based on converted reagents. The cyclotetrasiloxane was isolated by preparative g.l.c. and its H'n.m.r. spectrum was obtained in CCl$_4$ solution(δ) 0.0 (SiCH$_3$, 3H, s); 0.1 (SiCH$_3$, 12H, s); 0.3 (SiCH$_3$, 3H, s); 0.35 (SiCH$_3$, 3H, s); 5.75 (SiCH=CH$_2$, 3H, m).

That which is claimed is:

1. A method for preparing a cyclotetrasiloxane and an aliphatic chloride and/or an acyl chloride, said method comprising heating a mixture consisting essentially of
  (I) one molar portion of a silane-acyloxy component selected from the group consisting of
  (A) a silylhydrocarbonoxy acylate having the formula $R^1_aCl_{(3-a)}SiQO_2CR^2$, (B) a hydrocarbonoxy silylacylate having the formula $R^1{}_aCl_{(3-a)}SiQCO_2R^2$, and (C) a mixture of equimolar amounts of
  (i) a silane having the formula $R^1{}_bSiCl_{(4-b)}$ and
  (ii) an acyloxy compound selected from the group consisting
    of hydrocarbon carboxylic esters and hydrocarbon carboxylic anhydrides, wherein, at each occurrence,
    a denotes a number having a value of 0 or 1;
    b denotes a number having a value of 0, 1 or 2;
    $R^1$ denotes a monovalent substituted or unsubstituted hydrocarbon radical;
    $R^2$ denotes a monovalent unsubstituted hydrocarbon radical;
    Q denotes a divalent substituted or unsubstituted hydrocarbon radical; any hydrocarbon radical bonded to an oxygen atom of an acyloxy radical being bonded at an aliphatic carbon atom of said any hydrocarbon radical and
(II) at least one molar portion of a cyclotrisiloxane having the formula $(R^1{}_2SiO)_3$ wherein each $R^1$ denotes, independently, a monovalent substituted or unsubstituted hydrocarbon radical; said heating being sufficient to produce a cyclotetrasiloxane having the formula

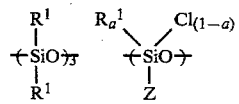

wherein $R^1$ and a are as denoted above and Z denotes a radical selected from the group consisting of $R^1$, Cl, QCOCl and QCl and at least one reaction product selected from the group consisting of an acyl chloride and an aliphatic chloride; the substituents of said substituted hydrocarbon radicals being non-reactive during said heating.

2. A method according to claim 1 wherein the silane-acyloxy component consists essentially of a silylhydrocarbonoxy acylate having the formula $R^1{}_aCl_{(3-a)}SiC_nH_{2n}O_2CR^2$ wherein n denotes a number having a value of from 2 to 4, said mixture being heated sufficiently to form an aliphatic chloride-substituted cyclotetrasiloxane reaction product having the formula

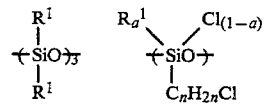

and an acyl chloride reaction product having the formula $R^2COCl$.

3. A method according to claim 2 wherein a has a value of 1 and each $R^1$ denotes, independently, a radical selected from the group consisting of hydrocarbon radicals having from 1 to 6 carbon atoms, and halogenated derivatives thereof, and $R^2$ denotes a lower alkyl radical.

4. A method according to claim 3 wherein the cyclotrisiloxane is hexamethylcyclotrisiloxane, the silane-acyloxy component is $CH_3(Cl)_2SiC_nH_{2n}O_2CR^2$ and the cyclotetrasiloxane reaction product is

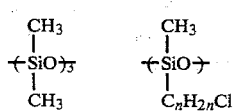

wherein $C_nH_{2n}$ denotes $-CH_2CH_2CH_2-$.

5. A method according to claim 1 wherein the silane-acyloxy component consists essentially of a hydrocarbonoxy silylacylate having the formula $R^1{}_aCl_{(3-a)}SiC_nH_{2n}CO_2R^2$ wherein n denotes a number having a value of from 2 to 4, said mixture being heated sufficiently to form an acid chloride-substituted cyclotetrasiloxane reaction product having the formula

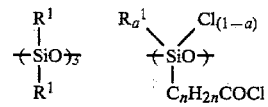

and an aliphatic chloride reaction product having the formula $R^2Cl$.

6. A method according to claim 5 wherein a has a value of 1 and each $R^1$ denotes, independently, a radical selected from the group consisting of hydrocarbon radicals having from 1 to 6 carbon atoms and halogenated derivatives thereof and $R^2$ denotes a lower alkyl radical.

7. A method according to claim 6 wherein the cyclotrisiloxane is hexamethylcyclotrisiloxane, the silane-acyloxy component is $CH_3(Cl)_2SiC_nH_{2n}CO_2R^2$ and the cyclotetrasiloxane reaction product is

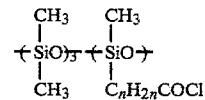

wherein $C_nH_{2n}$ denotes $-CH_2CH_2-$ or

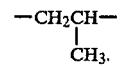

8. A method according to claim 1 wherein the silane-acyloxy component consists essentially of an equimolar mixture of
  (i) a silane having the formula $R^1{}_bSiCl_{(4-b)}$ wherein $R^1$ denotes a monovalent substituted or unsubstituted hydrocarbon radical and b has a value of 0, 1 or 2 and
  (ii) a hydrocarbon carboxylic ester having the formula $R^2CO_2R^2$, said mixture being heated sufficiently to form a cyclotetrasiloxane reaction product having the formula

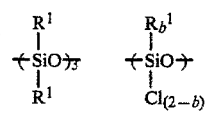

an acyl chloride reaction product having the formula $R^2COCl$ and an aliphatic chloride reaction product having the formula $R^2Cl$.

9. A method according to claim 8 wherein b has a value of 2 and each $R^1$ denotes, independently, a radical selected from the group consisting of hydrocarbon radicals having from 1 to 6 carbon atoms and halogenated derivatives thereof and $R^2$ denotes, independently, a lower alkyl radical.

10. A method according to claim 9 wherein the cyclotrisiloxane is hexamethylcyclotrisiloxane, the silane is $R^1CH_3SiCl_2$ and the cyclotetrasiloxane reaction product is

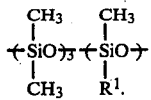

11. A method according to claim 10 wherein $R^1$ is selected from the group consisting of methyl, ethyl, vinyl, phenyl and 3,3,3-trifluoropropyl.

12. A method according to claims 1, 2, 3, 4, 5, 6, 7, 8 9, 10, or 11 wherein the mixture being heated comprises an amount of a halide salt wherein the halide portion is selected from chloride, bromide and iodide cations, said halide salt being present in sufficient amount and being sufficiently soluble in the mixture during said heating, to provide a catalytically effective amount of the halide salt dissolved in the mixture.

13. A method according to claim 12 wherein the halide salt is selected from quaternary ammonium halide salts, quaternary phosphonium halide salts and quaternary pyridinium halide salts.

14. A method according to claim 1 wherein the cyclotrisiloxane is hexamethylcyclotrisiloxanes and the cyclotetrasiloxane reaction product is

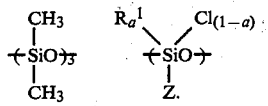

15. A cyclotetrasiloxane having the formula

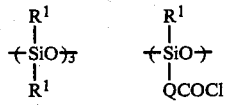

wherein each $R^1$ denotes, independently, a monovalent substituted or unsubstituted hydrocarbon radical and Q denotes a divalent substituted or unsubstituted hydrocarbon radical.

16. A cyclotetrasiloxane according to claim 15 wherein each $R^1$ denotes the methyl radical.

17. A cyclotetrasiloxane according to claim 16 wherein Q denotes an alkylene radical of the formula $-C_nH_{2n}-$ wherein n has a value of from 2 to 4.

18. A cyclotetrasiloxane according to claim 17 wherein the alkylene radical is $-CH_2CHCH_3$.

* * * * *